US012740524B2

(12) United States Patent
Saga et al.

(10) Patent No.: US 12,740,524 B2
(45) Date of Patent: Sep. 22, 2026

(54) HIGH-STEARIC ACID SUNFLOWER SEED

(71) Applicant: FUJI OIL CO., LTD., Izumisano (JP)

(72) Inventors: Hirohisa Saga, Tsukubamirai (JP); Masaharu Kato, Tsukubamirai (JP)

(73) Assignee: FUJI OIL CO., LTD., Izumisano (JP)

( * ) Notice: Subject to any disclaimer, the term of this patent is extended or adjusted under 35 U.S.C. 154(b) by 521 days.

(21) Appl. No.: 18/015,589

(22) PCT Filed: Jul. 26, 2021

(86) PCT No.: PCT/JP2021/027454
§ 371 (c)(1),
(2) Date: Jan. 11, 2023

(87) PCT Pub. No.: WO2022/024958
PCT Pub. Date: Feb. 3, 2022

(65) Prior Publication Data

US 2023/0247954 A1 Aug. 10, 2023

(30) Foreign Application Priority Data

Jul. 28, 2020 (JP) ................................ 2020-127157

(51) Int. Cl.

| | |
|---|---|
| ***A01H 6/14*** | (2018.01) |
| ***A01H 1/00*** | (2006.01) |
| ***A01H 1/06*** | (2006.01) |
| ***A01H 5/10*** | (2018.01) |

(52) U.S. Cl.
CPC ............ *A01H 6/1464* (2018.05); *A01H 1/06* (2013.01); *A01H 1/104* (2021.01); *A01H 5/10* (2013.01)

(58) Field of Classification Search
None
See application file for complete search history.

(56) References Cited

U.S. PATENT DOCUMENTS

| | | | |
|---|---|---|---|
| 7,141,267 | B2 | 11/2006 | Martinez Force et al. |
| 10,045,503 | B2 | 8/2018 | Gerdes et al. |
| 2008/0301837 | A1 | 12/2008 | Rommens et al. |
| 2018/0282711 | A1 | 10/2018 | Walsh et al. |

FOREIGN PATENT DOCUMENTS

| | | | |
|---|---|---|---|
| CN | 108902862 | A | 11/2018 |
| EP | 3395165 | A1 | 10/2018 |
| WO | 95020313 | A1 | 8/1995 |

OTHER PUBLICATIONS

Marek, L. F. (May 2016). Sunflower genetic resources. In Proceedings of the 19th international sunflower conference, Edirne, Turkey (vol. 29, pp. 31-44). (Year: 2016).*

(Continued)

*Primary Examiner* — Amjad Abraham
*Assistant Examiner* — Dequantarius Javon Speed
(74) *Attorney, Agent, or Firm* — MH2 Technology Law Group, LLP

(57) ABSTRACT

The problem solved by the present invention is to provide a high-stearic acid sunflower line. This problem is solved by a sunflower seed comprising a sequence insertion mutation on the 3' side from the TATA box and on the 5' side from the start codon of a stearoyl-acyl carrier protein desaturase 17 (SAD17) gene.

9 Claims, 5 Drawing Sheets

Specification includes a Sequence Listing.

(56) References Cited

OTHER PUBLICATIONS

Staton, S. E., Bakken, B. H., Blackman, B. K., Chapman, M. A., Kane, N. C., Tang, S., . . . & Burke, J. M. (2012). The sunflower (*Helianthus annuus* L.) genome reflects a recent history of biased accumulation of transposable elements. The plant journal, 72(1), 142-153. (Year: 2012).*

Tian, Y., Chen, K., Li, X., Zheng, Y., & Chen, F. (2020). Design of high-oleic tobacco (*Nicotiana tabacum* L.) seed oil by CRISPR-Cas9-mediated knockout of NtFAD2-2. BMC Plant Biology, 20, 1-12. (Year: 2020).*

Thorneycroft, D., Sherson, S. M., & Smith, S. M. (2001). Using gene knockouts to investigate plant metabolism. Journal of experimental botany, 52(361), 1593-1601. (Year: 2001).*

Pérez-Vich B, Velasco L, Muñoz-Ruz J, Fernández-Martínez JM. Inheritance of High Stearic Acid Content in the Sunflower Mutant CAS-14. Crop science. Jan. 2006;46(1):22-9. (Year: 2006).*

Russian Office Action issued in corresponding Russian Patent Application No. 2023104232/10(009175) dated Dec. 23, 2024, English language translation, 15 pages.

Affidavit of Dr. Andres Zambelli dated Jul. 19, 2021 cited in the Decision on Opposition dated Oct. 28, 2021 for corresponding Japanese Patent Application No. 2020-127157, 7 pages.

Appendix I, Base Sequence of the Promoter region of SAD17 gene of wild type sunflower and CAS3 variant submitted with Affidavit of Dr. Andres Zambelli dated Jul. 19, 2021 cited in the Decision on Opposition dated Oct. 28, 2021 for corresponding Japanese Patent Application No. 2020-127157), 2 pages.

Appendix II, Curriculum Vitae of Dr. Andres Zambelli, Jul. 14, 2021 (submitted with Affidavit of Dr. Andres Zambelli dated Jul. 19, 2021 cited in the Decision on Opposition dated Oct. 28, 2021 for corresponding Japanese Patent Application No. 2020-127157), 3 pages.

Cantisán, S., et al., "Enzymatic studies of high stearic acid sunflower seed mutants," Plant Physiology and Biochemistry, 2000, vol. 38, No. 5, pp. 377-382.

Hongtrakul, V., et al., "DFLP, SSCP, and SSR markers for Δ9-stearoyl-acyl carrier protein desaturases strongly expressed in developing seeds of sunflower: intron lengths are polymorphic among elite inbred lines," Molecular Breeding, 1998, vol. 4, pp. 195-203.

Hoshino, T., et al., "Molecular characterization of high stearic acid soybean mutants and post-transcriptional control of GmSACPD genes in the mutant with a single nucleotide deletion," Plant Gene, 2020, vol. 21, Article 100207, pp. 1-8.

International Search Report for International Application No. PCT/JP2021/027454 dated Sep. 21, 2021, 7 pages including English translation.

Japanese Decision on Opposition for corresponding Japanese Application No. 2020-127157 dated Oct. 28, 2021, 25 pages including English machine translation.

Japanese Notice of Reasons for Refusal for corresponding Japanese Application No. 2020-127157 dated Sep. 8, 2020, 11 pages including English machine translation.

Kuddus, R., et al., "Relationship between TATA-Binding Protein and Herpes Simplex Virus Type 1 ICP4 DNA-Binding Sites in Complex Formation and Repression of Transcription," Journal of Virology, 1995, vol. 69, No. 9, pp. 5568-5575.

Leopardi, R., et al., "Repression of the Herpes Simplex Virus 1 α4 Gene by Its Gene Product (ICP4) within the Context of the Viral Genome Is Conditioned by the Distance and Stereoaxial Alignment of the ICP4 DNA Binding Site Relative to the TATA Box," Journal of Virology, 1995, vol. 69, No. 5, pp. 3042-3048.

Michelmore, R. W., et al., "Texas blueweed ESTs from the Compositae Genome Project," (CHCM578.b1_C02.ab1 CHC(LMS) Texas blueweed Helianthus ciliaris cDNA clone CHCM578, mRNA sequence), GenBank Accession No. EL426324, Version EL426324.1, Nov. 27, 2007, 1 page.

Osorio, J., et al., "Mutant Sunflowers with High Concentration of Saturated Fatty Acids in the Oil," Crop Science, 1995, vol. 35, p. 739-742.

Pérez-Vich, B., et al., "Genetic Relationships between Loci Controlling the High Stearic and the High Oleic Acid Traits in Sunflower," Crop Science, 2000, vol. 40, pp. 990-995.

Pérez-Vich, B., et al., "Stearoyl-ACP and oleoyl-PC desaturase genes cosegregate with quantitative trait loci underlying high stearic and high oleic acid mutant phenotypes in sunflower," Theoretical and Applied Genetics, 2002, vol. 104, pp. 338-349.

Rousselin, P., et al., "Modification of sunflower oil quality by seed-specific expression of a heterologous A9-stearoyl-(acyl carrier protein) desaturase gene," Plant Breeding, 2002, vol. 121, No. 2, pp. 108-116.

Salas, J. J., et al., "The biochemical characterization of a high-stearic acid sunflower mutant reveals the coordinated regulation of stearoyl-acyl carrier protein desaturases," Plant Physiology and Biochemistry, 2008, vol. 46, pp. 109-116.

"CHWM10344.b1_P18.ab1 CHW(LMS) silverleaf sunflower Helianthus argophyllus cDNA clone CHWM10344, mRNA sequence", Database EMBL, Accession No. EE613216, Aug. 25, 2006, 1 page.

Supplementary European Search Report and Search Opinion dated Jul. 22, 2024 for corresponding European Patent Application No. 21849529.9, 9 pages.

* cited by examiner

Fig. 1
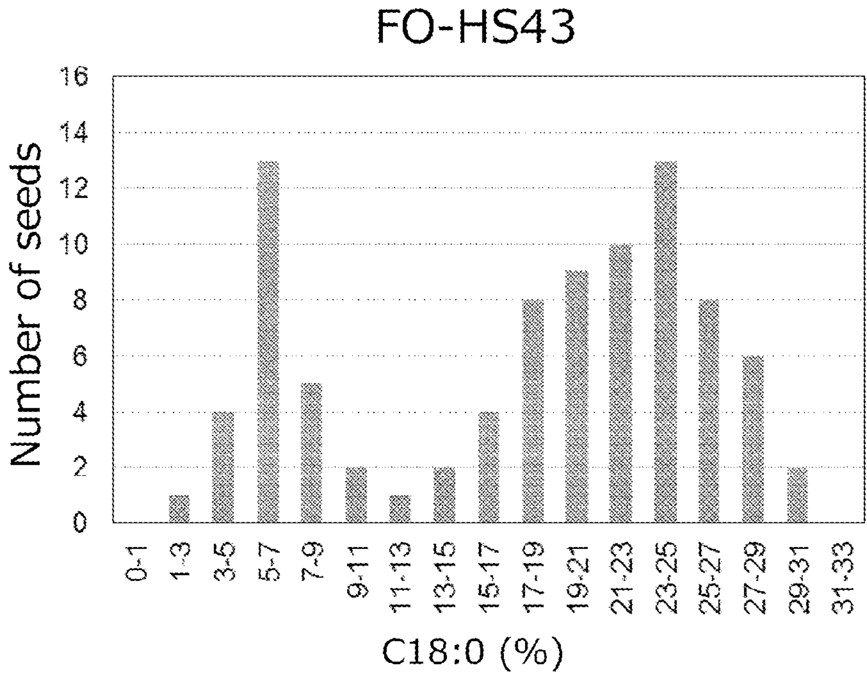
Fig. 2
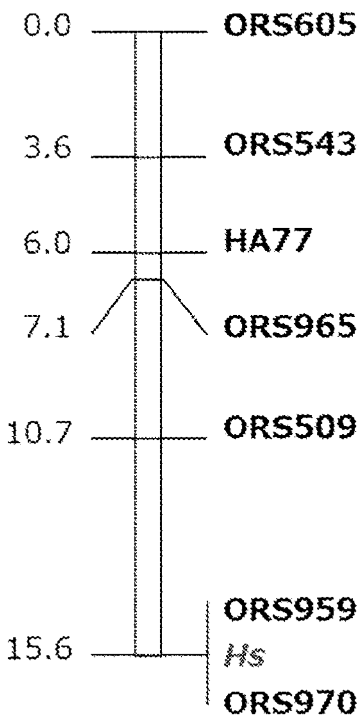

HIGH-STEARIC ACID SUNFLOWER SEED

CROSS-REFERENCE TO RELATED APPLICATIONS

This application is a U.S. National Stage application of PCT/JP2021/027454 filed 26 Jul. 2021, which claims priority to Japanese application No. 2020-127157 filed 28 Jul. 2020, the entire disclosures of which are hereby incorporated by reference in their entireties.

SEQUENCE LISTING

The present application contains a Sequence Listing which has been submitted electronically in ASCII format and is hereby incorporated by reference in its entirety. Said ASCII copy, created on 11 Jan. 2023, is named 0223_0100-PCT-US_Sequence_Listing.txt and is 10 kilobytes in size.

TECHNICAL FIELD

The present invention relates to sunflower seeds, etc.

BACKGROUND ART

Sunflowers are important and useful agricultural products that provide food for humans and livestock.

Sunflowers are typically grown to produce oil. The obtained fats and oils are mainly composed of unsaturated fatty acids, such as linoleic acid (18:2) and oleic acid (18:1), and partially composed of palmitic acid (16:0), stearic acid (18:0), arachidic acid (20:0), and behenic acid (22:0). The stearic acid content in the fatty acid composition of sunflower fats and oils is typically 10% or less, and usually 3 to 7%.

Conventionally, sunflowers are oil crops; fats and oils obtained from sunflower seeds have a linoleic acid content as high as 50 to 70% in the fatty acid composition. So far, many mutants have been obtained by modifying the fatty acid composition through chemical mutagenesis using ethyl methanesulfonate or sodium azide, or radiation mutagenesis using X-rays or γ-rays.

At present, the most prevalent fatty acid mutants of sunflower include high-oleic acid sunflower having an oleic acid content of 75 to 90% and a linoleic acid content of 2 to 10%. High-oleic acid sunflower oil with a high oleic acid content is a liquid fat with excellent stability that is useful for frying and for storage.

On the other hand, since most fats and oils obtained from plants are liquid fats rich in unsaturated fatty acids, there is a worldwide shortage of solid fats. Solid fats are essential as raw materials for many food industry products, such as margarine, shortening, fillings, and fats and oils for confectioneries.

Although solid fats can be produced by hydrogenation for hardening vegetable fats and oils rich in unsaturated fatty acids, there is a problem in that trans-fatty acids, which cause health problems, are produced as a by-product. Against this background, natural vegetable solid fats are in demand to replace hydrogenated fats and oils in the food industry.

CITATION LIST

Non-Patent Literature

NPL 1: Osorio J, Fernandez-Martinez J, Mancha M, Garces R. Mutant sunflowers with high concentration of saturated fatty acids in the oil; Crop Sci 1995; 35: 739-742.

NPL 2: Hongtrakul V, Slabaugh M B, Knapp S J. DFLP, SSCP, and SSR markers for Δ9-stearoyl-acyl carrier protein desaturases strongly expressed in developing seeds of sunflower: Intron lengths are polymorphic among elite inbred lines; Mol Breed 1998; 4: 195-203.

SUMMARY OF INVENTION

Technical Problem

The present inventors focused on the use of high-stearic acid sunflower oil for the purpose of efficiently producing solid lipids.

Non-patent literature (NPL) 1 reports high-stearic acid sunflower (CAS-3). The high-stearic acid trait in CAS-3 is controlled by partially recessive alleles (es1, es2) at two independent loci, Es1 and Es2. However, the specific genes thereof and the mode of mutation are unclear, making it difficult to efficiently transmit the trait to future generations or to efficiently obtain lines with other traits in addition to this trait through improvement of breeding.

An object of the present invention is to provide a high-stearic acid sunflower line.

Solution to Problem

The present inventors conducted extensive research and consequently found that the above object can be achieved by sunflower seeds having a sequence insertion mutation on the 3' side from the TATA box and on the 5' side from the start codon of a stearoyl-acyl carrier protein desaturase 17 (SAD17) gene. The present inventors conducted further research based on the findings to accomplish the present invention. More specifically, the present invention encompasses the following embodiments.

Item 1. A sunflower seed comprising a sequence insertion mutation on a 3' side from a TATA box and on a 5' side from a start codon of a stearoyl-acyl carrier protein desaturase 17 (SAD17) gene.

Item 2. The sunflower seed according to Item 1, wherein the sequence is 100 to 1200 bases long.

Item 3. The sunflower seed according to Item 1, wherein the sequence is 400 to 800 bases long.

Item 4: The sunflower seed according to any one of Items 1 to 3, wherein the sequence comprises (a) or (b) below:

(a) the base sequence represented by SEQ ID NO: 1, or (b) a base sequence having at least 80% identity with the base sequence represented by SEQ ID NO: 1.

Item 5. The sunflower seed according to Item 4, wherein the identity is at least 90%.

Item 6. The sunflower seed according to any one of Items 1 to 5, wherein the sequence insertion mutation is introduced into a high-oleic acid sunflower line.

Item 7. The sunflower seed according to any one of Items 1 to 6, having a fatty acid composition having a stearic acid content of 11% or more.

Item 8. The sunflower seed according to any one of Items 1 to 7, comprising the sequence insertion mutation in both chromosome pair.

Item 9. The sunflower seed according to any one of Items 1 to 8, wherein the sunflower seed comprises the sequence insertion mutation on a 3' side from a TATA box and on a 5' side from a start codon of the base sequence represented by SEQ ID NO: 2 of the stearoyl-acyl carrier protein desaturase 17 (SAD17) gene, wherein the sequence is 400 to 800 bases long, and wherein the sunflower seed has a stearic acid content higher than the stearic acid content of sunflower seeds without the sequence insertion mutation.

Item 10. The sunflower seed according to any one of Items 1 to 9, which is a seed of FO-HS43 line (International Patent Organism Depositary Accession Number: IPOD FERM BP-22390) or a seed of a derivative line thereof.

Item 11. A sunflower plant comprising or for producing the sunflower seed of any one of Items 1 to 10.

Item 12. A sunflower plant obtained by germinating and growing the sunflower seed of any one of Items 1 to 10.

Item 13. A method for producing a lipid, comprising collecting a lipid from the sunflower seed of any one of Items 1 to 10.

Advantageous Effects of Invention

The present invention provides a high-stearic acid sunflower line.

BRIEF DESCRIPTION OF DRAWINGS

FIG. 1 is a frequency distribution graph showing the stearic acid content in the fatty acid composition of seeds of M2 population of the FO-HS43 line. The vertical axis shows the number of seeds, and the horizontal axis shows the stearic acid content in the fatty acid composition of the seeds.

FIG. 2 shows the results of mapping of high-stearic acid (Hs) locus based on linkage analysis. LG1 represents the first chain group.

DESCRIPTION OF EMBODIMENTS

Figure 3:
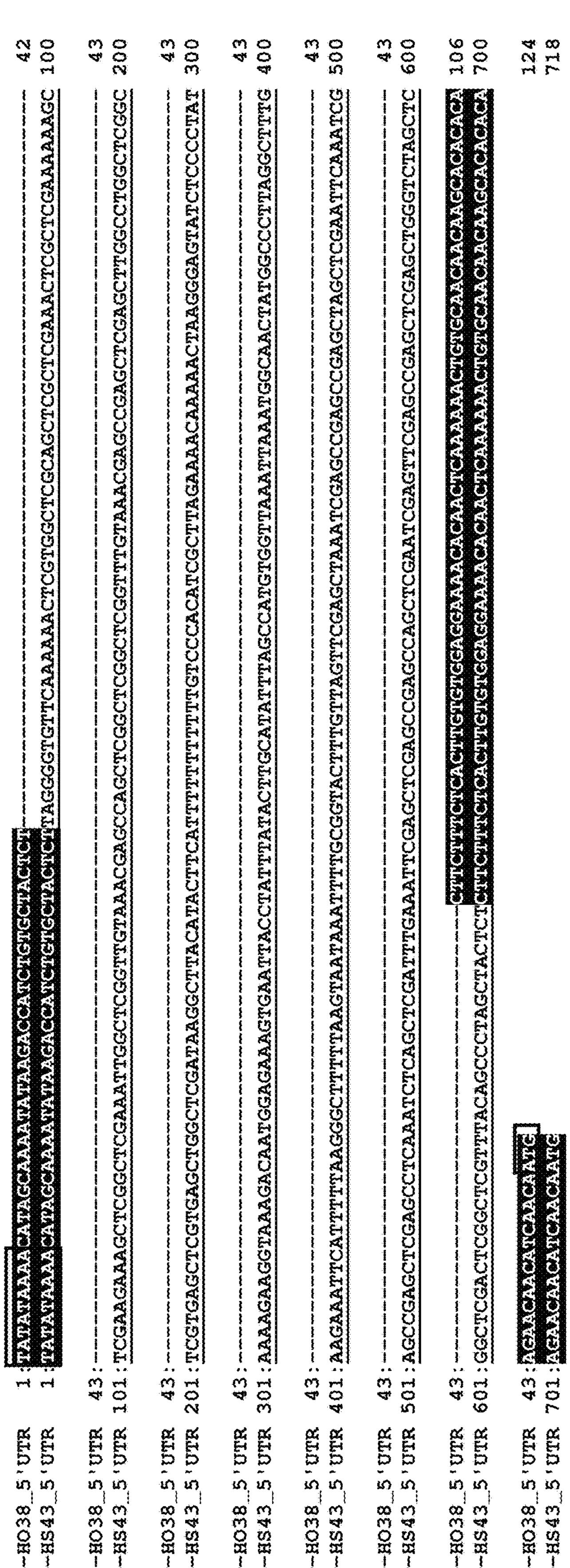
FIG. 3 shows part of gene sequences around the 5' UTR of the stearoyl-acyl carrier protein desaturase 17 (SAD17) of the high-oleic acid sunflower line FO-HO38 and the high stearic acid sunflower line FO-HS43 (FO-HO38: SEQ ID NO: 2, FO-HS43: SEQ ID NO: 3). The area framed at the left end of the first two lines (nucleotides 1-9 of SEQ ID NO: 2 and SEQ ID NO: 3) shows sequences that are presumed to be TATA boxes, and the ATG sequence framed at the end of the last line of SEQ ID NO: 2 shows the translation start codon of the SAD17. The area underlined is the insertion sequence in FO-HS43.

In the present specification, the expressions "comprise," "include," and "contain" include the concepts of comprising, containing, consisting essentially of, and consisting of.

1. Sunflower Seed and Sunflower Plant

In one embodiment, the present invention relates to sunflower seeds comprising a sequence insertion mutation on the 3' side from the TATA box and on the 5' side from the start codon of a stearoyl-acyl carrier protein desaturase 17 (SAD17) gene (also referred to herein as "the sunflower seed of the present invention"). The details are described below.

The seed oil of sunflower (*Helianthus annuus*) contains about 5% of stearic acid, and the stearic acid is desaturated to oleic acid by Δ9-stearoyl-acyl carrier protein desaturases (SAD). Attempts have been made so far to identify sunflower SAD genes, and two SAD gene sequences (SAD6 and SAD17) have been isolated as full-length cDNAs that are strongly expressed at the seed developmental stage (NPL 2).

In various sunflowers, the base sequence and amino acid sequence of the SAD17 gene are known, or can be readily determined based on a known base sequence or amino acid sequence of the SAD17 gene (e.g., by analysis of identity with these sequences). For example, the SAD17 gene is the gene identified by NCBI Gene ID: U91340, the amino acid sequence of the SAD17 gene is the amino acid sequence (SEQ ID NO: 12) identified by NCBI RefSeq accession number: XP_021982111, and the mRNA sequence of the SAD17 gene is the base sequence (SEQ ID NO: 13) identified by NCBI RefSeq accession number: XM_022126419.

The SAD17 gene targeted by the present invention includes naturally occurring variants. The SAD17 gene targeted by the present invention may have base mutations, such as substitution, deletion, addition, and insertion, for example, in the promoter and/or coding regions, as long as the desaturase activity of the protein encoded by the target gene is not significantly impaired. The mutations are preferably a mutation that does not result in amino acid substitution in the protein translated from the mRNA, or preferably a mutation that causes conservative substitution of an amino acid.

In the present specification, "conservative substitution" refers to the substitution of an amino acid residue with another amino acid residue with a similar side chain. For example, substitution between amino acid residues each having a basic side chain such as lysine, arginine, or histidine is conservative substitution. The following substitution is also considered to be conservative substitution: substitution between amino acid residues with an acidic side chain such as aspartic acid or glutamic acid; substitution between amino acid residues with an uncharged polar side chain such as glycine, asparagine, glutamine, serine, threonine, tyrosine, or cysteine; substitution between amino acid residues with a nonpolar side chain such as alanine, valine, leucine, isoleucine, proline, phenylalanine, methionine, or tryptophan; substitution between amino acid residues with a p-branched side chain such as threonine, valine, or isoleucine; and substitution between amino acid residue with an aromatic side chain such as tyrosine, phenylalanine, tryptophan, or histidine.

For example, the amino acid sequence of the protein encoded by the SAD17 gene targeted by the present invention has, for example, at least 95%, preferably at least 98%, and more preferably at least 99% identity with the amino acid sequence of the protein encoded by the wild-type SAD17 gene of the same line. Further, for example, the amino acid sequence of the protein encoded by the SAD17 gene targeted by the present invention is identical to the amino acid sequence of the protein encoded by the wild-type SAD17 gene of the same line; or has one, or two or more (e.g., 2 to 10, preferably 2 to 5, more preferably 2 to 3, and still more preferably 2) substitutions, deletions, additions, or insertions in this amino acid sequence.

The "identity" of amino acid sequences refers to the degree to which two or more contrastable amino acid sequences match each other. Thus, the greater the degree of match between two amino acid sequences, the greater the identity or similarity of those sequences. The degree of the identity of amino acid sequences can be determined by using, for example, FASTA, a tool for sequence analysis, with default parameters. Alternatively, the degree of identity of amino acid sequences can be determined by using BLAST, an algorithm by Karlin and Altschul (Karlin S, Altschul S F. Methods for assessing statistical significance of molecular sequence features by using general scoring schemes. Proc Natl Acad Sci USA. 87, pp. 2264-2268 (1990), and Karlin S, Altschul S F. Applications and statistics for multiple high-scoring segments in molecular sequences. Proc Natl Acad Sci USA. 90:5873-7 (1993)). A program called "BLASTX" has been developed based on the BLAST algorithm. The specific techniques of these analysis methods are known and can be found at the National Center of Biotechnology Information (NCBI) website. The "identity" of base sequences is also defined according to the above description.

The sunflower seed of the present invention comprises a sequence insertion mutation on the 3' side from the TATA box and on the 5' side from the start codon of the SAD17 gene targeted by the present invention described above.

The sequence for insertion is preferably 100 to 1200 bases long, more preferably 200 to 1000 bases long, still more preferably 400 to 800 bases long, even more preferably 500 to 700 bases long, and particularly preferably 550 to 650 bases long.

The sequence for insertion preferably comprises, for example, (a) or (b) below:

(a) the base sequence represented by SEQ ID NO: 1, or (b) a base sequence having at least 80% identity with the base sequence represented by SEQ ID NO: 1.

The identity in the base sequence (b) is preferably at least 85%, more preferably at least 90%, still more preferably at least 95%, even more preferably at least 98%, and particularly preferably at least 99%.

The site at which the sequence for insertion is inserted is not limited as long as it is located on the 3' side from the TATA box and on the 5' side from the start codon of the SAD17 gene. For example, the TATA box is a sequence (TATATAAAA) between the first base and the ninth base from the 5' of the base sequence represented by SEQ ID NO: 2, which represents a partial SAD17 gene sequence. The phrase "on the 3' side from a TATA box" means on the 3' side from the base at the 3' end of the TATA box. For example, the start codon is a sequence between the 122nd base and the 124th base from the 5' of the base sequence represented by SEQ ID NO: 2, which represents a partial SAD17 gene sequence. The phrase "on the 5' side from a start codon" means on the 5' side from the base at the 5' end of the start codon. In one embodiment of the present invention, the site at which the sequence for insertion is inserted is on the 3' side from the TATA box and on the 5' side from the start codon of the base sequence represented by SEQ ID NO: 2 of the SAD17 gene. For example, in the base sequence represented by SEQ ID NO: 2, which represents a partial SAD17 gene sequence, the site at which the sequence is inserted is preferably the site from the 15th base to 102nd base from the 5' of the sequence, more preferably the site from the 25th base to 82nd base from the 5' of the sequence, still more preferably the site from the 30th base to 62nd base from the 5' of the sequence, and even more preferably the site from the 35th base to 52nd base from the 5' of the sequence. Various mutations (e.g., substitution, deletion, addition, or insertion of 1 to 30 (preferably 1 to 20, and more preferably 1 to 10) bases long) associated with the insertion may be present near the inserted sequence. Preferable examples of such a mutation include insertion of the sequence consisting of GCTACTCT.

In the sunflower seed of the present invention, it is preferred that the chromosome pair both have a sequence insertion mutation. However, even when one of the chromosome pair has a sequence insertion mutation, the object is achieved.

In the sunflower seed of the present invention, the introduction of the mutation reduces the accumulation of SAD17 gene transcripts. In the sunflower seed of the present invention, the amount of accumulation of SAD17 gene transcripts (including both from genes with the insertion sequence and from genes without the insertion sequence) is, for example, 50% or less, preferably 40% or less, more preferably 30% or less, still more preferably 20% or less, and even more preferably 10% or less, with respect to the same amount of accumulation in sunflower seeds of the line before introduction of the sequence insertion mutation. In a preferred embodiment of the sunflower seed of the present invention, the introduction of the mutation reduces the amount of accumulation of SAD6 gene transcripts. In the sunflower seed of the present invention, the amount of accumulation of SAD6 gene transcripts is, for example, 90% or less, preferably 80% or less, and more preferably 70% or less, with respect to the same amount of accumulation in sunflower seeds of the line before introduction of the sequence insertion mutation. The amount of accumulation of gene transcripts can be quantified by quantitative RT-PCR analysis using RNA extracted from seeds at the developmental stage (e.g., 10 days after flowering (DAF)).

The sunflower seed of the present invention has a fatty acid composition having a stearic acid content of, for example, 11% or more, preferably 15% or more, more preferably 20% or more, and still more preferably 25% or more. The upper limit is not limited, and is, for example, 40%, 35%, or 33%. In the present specification, % fatty acid refers to a percent by weight of fatty acids as a component of a lipid. The "fatty acid composition" means the composition of fatty acid residues constituting a lipid.

The sunflower seed of the present invention may also have a mutation other than the sequence insertion mutation described above. For example, in a preferred embodiment of the present invention, the sunflower seed of the present invention is a sunflower seed obtained by introducing the sequence insertion mutation described above into a high-oleic acid sunflower line. The high-oleic acid sunflower lines are not limited, and are sunflower lines having an oleic acid content in the seed of, for example, 60% or more, preferably 70% or more, and more preferably 80% or more.

Specific examples of the sunflower seed of the present invention include seeds of the FO-HS43 line (International Patent Organism Depositary Accession Number: IPOD FERM BP-22390) and seeds of derivative lines thereof. The seeds of derivative lines thereof are not limited as long as they are seeds of lines obtained by crossing the seeds of the FO-HS43 line. Examples include seeds of lines obtained by self-crossing of the seeds of the FO-HS43 line, seeds obtained by crossing the seeds of the FO-HS43 line with seeds of other lines, and seeds of generations n+1 to m (wherein n and m each represent any integer, for example, 1 to 50) with the above seeds being generation n.

The sunflower seed of the present invention has a higher stearic acid content in the fatty acid composition than that of sunflower seeds (control sunflower seeds) without the sequence insertion mutation (the sequence insertion mutation on the 3' side from the TATA box and on the 5' side from the start codon of the stearoyl-acyl carrier protein desaturase 17 (SAD17) gene). For example, the stearic acid content in the fatty acid composition of the sunflower seed of the present invention is, for example, 2% or more, 3% or more, 4% or more, 5% or more, 6% or more, 7% or more, 8% or more, 9% or more, or 10% or more higher than the stearic acid content in the fatty acid composition of the control sunflower seeds.

In one embodiment, the present invention, in part, relates to sunflower plants comprising or for producing the sunflower seed of the present invention, and sunflower plants obtained by germinating and growing the sunflower seed of the present invention (these may be collectively referred to as "the sunflower plant of the present invention"). The phrase "comprising the sunflower seed of the present invention" means that it comprises the produced sunflower seed of the present invention in the flower, and the phrase "for producing the sunflower seed of the present invention" means that it is for producing the sunflower seed of the present invention by growing.

The sunflower plant means not only a plant at any stage of development, but also any plant part that can be attached to or separated from an intact whole plant. Such plant parts include, but are not limited to, plant organs, tissues, and cells. Specific examples of plant parts include stem, leave, root, inflorescence, flower, floret, fruit, pedicle, peduncle, stamen, anther, stigma, style, ovary, petal, sepal, carpel, root tip, root cap, root hair, leaf hair, seed hair, pollen particle, microspore, cotyledon, hypocotyl, epicotyl, xylem, phloem, parenchyma, albumen, companion cell, and guard cell; and any other known plant organs, tissues, and cells.

The sunflower seed of the present invention and the sunflower plant of the present invention may be obtained based on or in accordance with known methods. For example, the sunflower seed of the present invention and the sunflower plant of the present invention may be obtained by using *agrobacterium* methods, particle gun methods, protoplast methods, genome editing techniques, etc. Alternatively, the sunflower seed of the present invention and the sunflower plant of the present invention may be created by crossing the FO-HS43 line or a derivative line thereof.

The sunflower seed of the present invention and the sunflower plant of the present invention show a dominantly inherited high-stearic acid trait. In the present invention, dominance means that the inheritance mode is not recessive; incomplete dominance is included in dominance in the present invention.

2. Method for Producing Lipid

In one embodiment, the present invention relates to a method for producing a lipid, comprising collecting a lipid from the sunflower seed of the present invention (the method of which may be referred to as herein as "the production method of the present invention"). The details are described below.

In the production method of the present invention, the sunflower seed of the present invention is used as an oilseed. The sunflower seed of the present invention may be obtained after pretreatment, such as drying treatment and crushing treatment, if necessary.

The collecting method may be any method as long as a lipid can be collected from sunflower seeds. Examples of the collecting method include squeezing methods, solvent extraction methods, and methods in which these methods are combined. In a squeezing method, seeds are physically squeezed by applying pressure to thus collect a lipid. In a solvent extraction method, a solvent is added to seeds to transfer the oil content in the seeds to the solvent, and the solvent in which the oil content is dissolved is separated into a volatile solvent and an oil with a distillation apparatus to thus collect a lipid.

The collected lipid (crude oil) may be further subjected to purification treatment. Impurities contained in the crude oil, such as gummy matter, free fatty acids, pigments, odorous substances, and fine foreign substances, may be removed as necessary. Examples of the purification treatment include a degumming treatment, a deoxidizing treatment, a decolorizing treatment, a dewaxing treatment, and a deodorizing treatment.

The obtained lipid can be used as sunflower oil for various applications. Further, the obtained lipid can be used as a raw material for producing an SOS source of a lipid as a substitute for cacao butter.

3. Others

In one embodiment, the present invention relates to a method for producing sunflower seeds in which the distribution of saturated fatty acids in terms of different triglyceride molecular species is modified, compared with wild-type seeds. This method comprises a step of treating parent seeds for a sufficient period of time to induce one or more mutations in genetic traits that are involved in the biosynthesis of triglycerides by using a sufficiently powerful mutagenesis method. The method increases the stearic acid content. Examples of mutagenesis treatments include mutagenesis treatments that use a mutagenic agent, such as sodium azide or an alkylating agent, and mutagenesis treatments that use X-ray or y-ray radiation. Alternatively, other mutagenesis treatments that produce the same or similar effects as those of the above agents may also be used.

EXAMPLES

The present invention is described in detail below based on Examples; however, the present invention is not limited by these Examples.

Test Example 1. Creation of High-Stearic Acid Sunflower Mutant 14000 seeds of the high-oleic acid sunflower line FO-HO38 was irradiated with a carbon ion beam ($^{12}C^{6+}$, energy: 320 MeV, dose: 5 Gy) to obtain seeds of a first-generation mutant (M1). The M1 seeds were grown and self-pollinated to obtain M2 seeds of at least 3000 lines. The M2 seeds of each line were subjected to gas chromatography to analyze the fatty acid composition of individual seeds, and a single line of seeds with a high stearic acid content was selected. FIG. 1 is a frequency distribution graph of the stearic acid content in the M2 seed population of this line. FIG. 1 shows two distinct peaks, indicating that about 28% of the seeds (25/88 seeds) had a low stearic acid content (less than 11%), which is almost the same as the stearic acid content of the original line (FO-HO38) (about 5%), while about 72% of the seeds (63/88 seeds) had a high stearic acid content (11% or more). The seed with a high stearic acid content was selected, and the offspring were grown for five generations; the results confirmed that the stearic acid content was stably maintained. This line was named "FO-HS43 line" and deposited at the International Patent Organism Depositary, National Institute of Technology and Evaluation (IPOD, Room 120, 2-5-8, Kazusakamatari, Kisarazu, Chiba, 292-0818 Japan) (deposit number: IPOD FERM BP-22390, deposit date: Apr. 23, 2020).

According to Mendelian inheritance, if a mutation that occurred in M1-generation seeds (probabilistically, in only one of the chromosome pair) is inherited to the M2 generation via self-pollination, then, in the M2-generation seeds, the ratio of seeds without the mutation in both chromosome pair (+/+):seeds with the mutation in only one of the chromosome pair (+/mt):seeds with the mutation in both chromosome pair(mt/mt) is 1:2:1. In this case, if the trait produced by the mutation is a dominant trait, the seeds with this trait should account for about 75% (3 (the sum of +/mt and mt/mt)/4 (the sum of +/+, +/mt, and mt/mt)). The above results indicated that the seeds with a high stearic acid content accounted for about 72%, and thus suggested that the high-stearic acid trait produced by the mutation in the seeds was a dominant mutant trait.

If this is true, it may be possible to create isogenic hybrids of different fatty acid composition groups by using this genetic mutation in either heterozygous or homozygous form, which can be further expanded to the use of good genetic resources.

To confirm this point, the FO-HS43 line was crossed with a low-stearic acid line (FO-HO13 line with a stearic acid content of about 3 to 5%). The analysis results of the fatty acid composition of the produced F1 seeds showed that the seeds all had a stearic acid content of 15% or more. These results indicated that the high-stearic acid trait in the FO-HS43 line was a dominant trait; the dominant mutant allele with a high stearic acid content was named "Hs."

Test Example 2: Identification of High-Stearic Acid Gene Hs

To clarify the Hs locus in FO-HS43, FO-HS43 was crossed with the HA89 line, and a linkage analysis was conducted using the F2 population. As a result, the Hs locus was mapped to one end of the first linkage group (LG1) and located near the SSR markers ORS959 and ORS970 (FIG. 2).

Since LG1 contains a stearoyl-acyl carrier protein desaturase 17 (SAD17) gene, the sequence near the SAD17 gene of FO-HS43 was analyzed in detail. The results confirmed the insertion of a 586-bp sequence (SEQ ID NO: 1), which is not found in FO-HO38, on the 3' side from the TATA box and on the 5' side from the start codon of the SAD17 gene (FIG. 3).

The fact that the insertion was found downstream of the TATA box sequence (TATATAAAA) suggested that the insertion sequence may also be transcribed. Thus, the SAD17 transcripts in FO-HS43 were isolated, which confirmed a production of a long SAD17 transcript (mutant SAD17) containing a part of the insertion sequence.

Figure 4:
FIG. 4 is an electropherogram showing the results of PCR using a primer set for flanking the insertion sequence upstream of the 5' UTR of the SAD17 in FO-HS43. Bands for wild-type SAD17 (lower arrow) and for mutant SAD17 having a sequence insertion (upper arrow) were confirmed. Hs represents a dominant mutant (with a sequence insertion) allele, and hs represents a wild-type allele.
Figure 4:
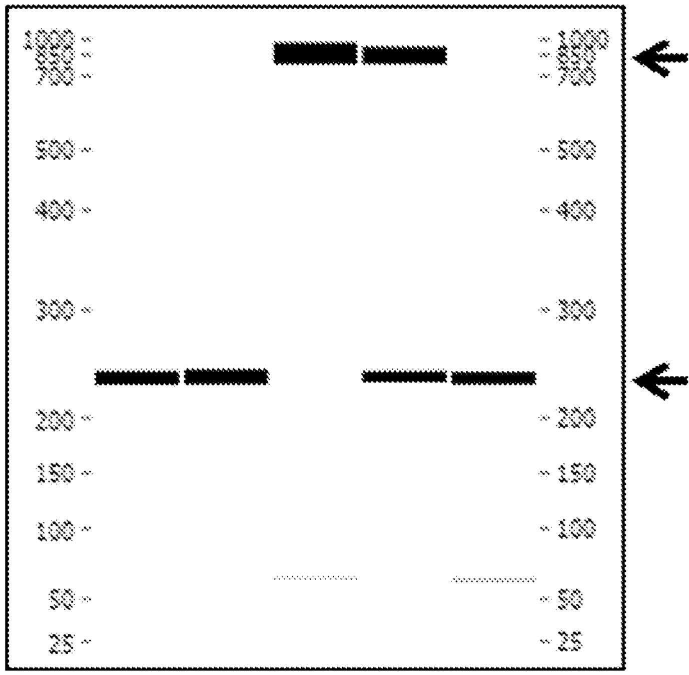
Figure 5:
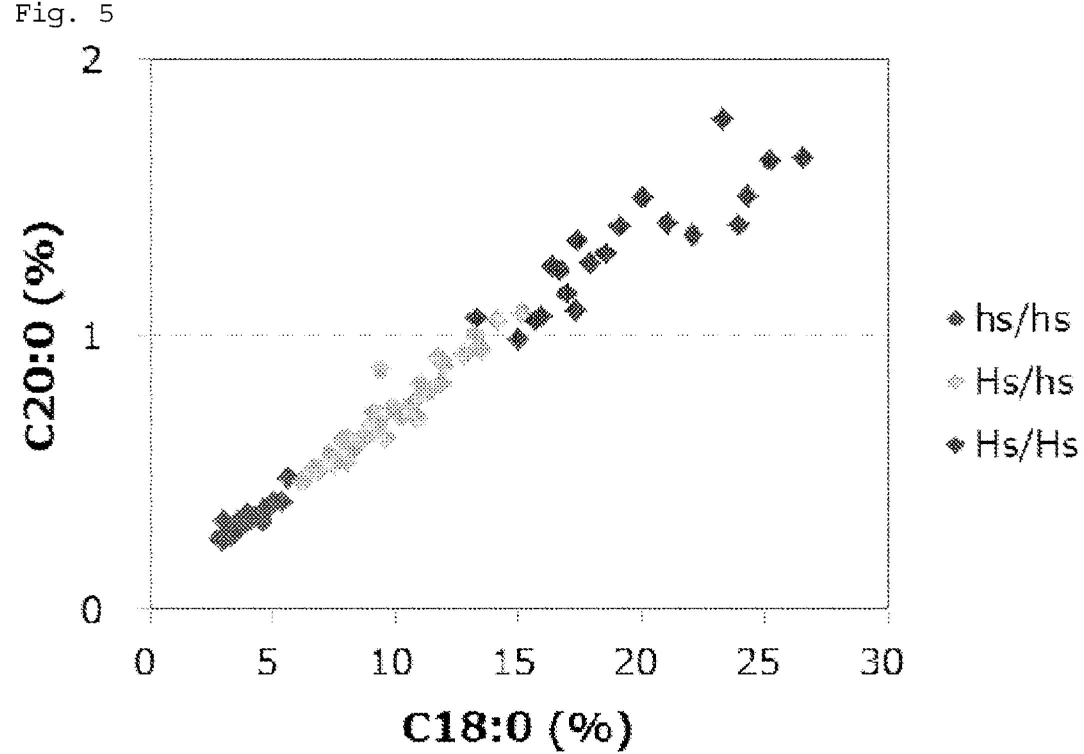
FIG. 5 is a graph showing the fatty acid content and Hs genotypes in each mature seed. The vertical axis shows the arachidic acid content in the fatty acid composition, and the horizontal axis shows the stearic acid content in the fatty acid composition. Hs/Hs is homozygous for the dominant mutant (with a sequence insertion) allele, Hs/hs is heterozygous for the dominant mutant allele, and hs/hs is homozygous for a wild-type allele.

Confirmation was made by PCR using a primer set (Forward: SEQ ID NO: 4; Reverse: SEQ ID NO: 5) for flanking the above insertion sequence of the SAD17 in FO-HS43. As a result, the presence of the insertion sequence (Hs allele) and the absence of the insertion sequence (hs allele) were detected, indicating that the use of this primer set was possible as a codominant marker for readily determining the Hs gene genotypes (mutant Hs homozygous, mutant Hs heterozygous, or wild-type hs homozygous) (FIG. 4). Further, the Hs genotypes determined by this method showed a high correlation with a stearic acid content (FIG. 5).

Figure 6:
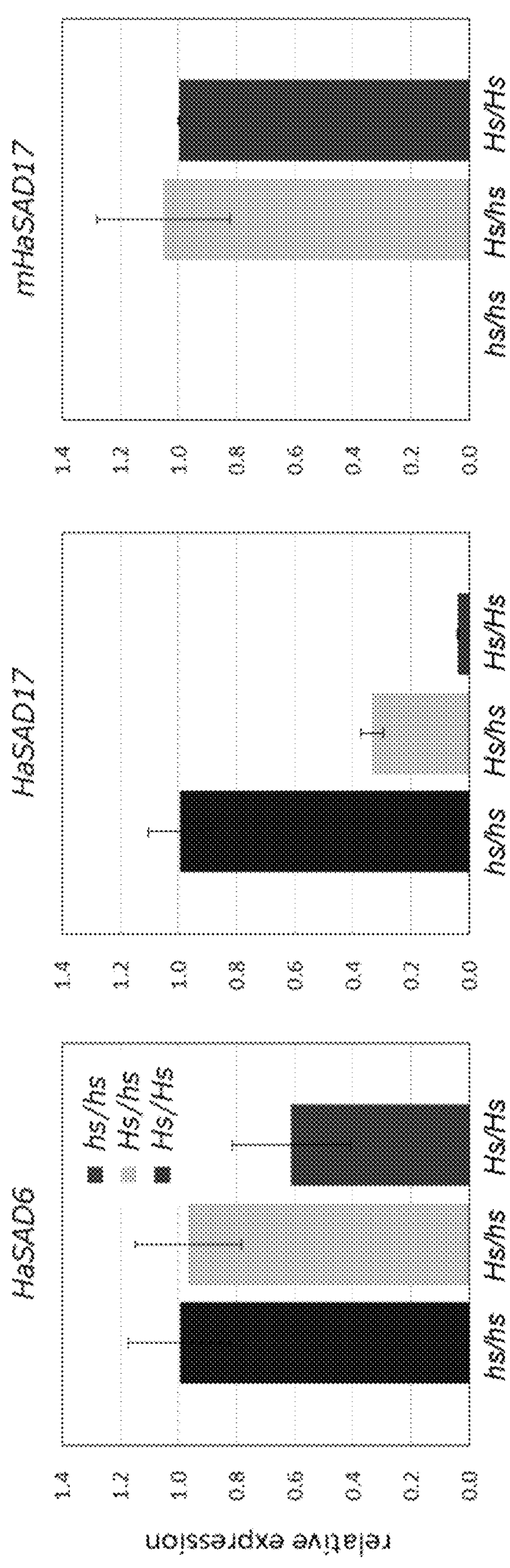
FIG. 6 is graphs showing measurement results of the amount of accumulation of SAD gene transcripts in seeds at the developmental stage (10 days after pollination). Hs/Hs is homozygous for the dominant mutant (with a sequence insertion) allele, Hs/hs is heterozygous for the dominant mutant allele, and hs/hs is homozygous for a wild-type allele. The vertical axis shows relative values of the accumulation amount. The graphs show the measurement results of the SAD6 gene, the SAD17 gene (both wild-type SAD17 and mutant SAD17), and the mutant SAD17 gene (mutant SAD17 only) from the left.

The seeds at the developmental stage (10 days after pollination) were subjected to quantitative RT-PCR to determine the amount of accumulation of SAD gene transcripts. The primer sets used here were as follows: primers for detection of the SAD6 gene (Forward: SEQ ID NO: 6, Reverse: SEQ ID NO: 7), primers for detection of the SAD17 gene (both wild-type SAD17 and mutant SAD17) (Forward: SEQ ID NO: 8, Reverse: SEQ ID NO: 9), and primers for detection of the mutant SAD17 gene (mutant SAD17 only) (Forward: SEQ ID NO: 10, Reverse: SEQ ID NO: 11). The results confirmed that the accumulation of SAD17 gene transcripts was hardly detected in the mutant Hs homozygous individuals (Hs/Hs), and that the accumulation amount in the mutant Hs heterozygous individuals (Hs/hs) also reduced to equal to or less than half of that of the wild type (hs/hs) (FIG. 6). In terms of the mutant Hs homozygous individuals, the results also showed a trend toward a reduction in the accumulation of transcripts of SAD6, which is a homologous gene of SAD17. These results were consistent with the results of the Hs genotypes and the stearic acid content in the seeds, indicating that the expression of the trait with a high stearic acid content in FO-HS43 was due to efficient SAD gene expression inhibition achieved by the insertion sequence on the 3' side from the TATA box and on the 5' side from the start codon of the SAD17 gene.

Sequence Listing:

P21-066WO_PCT_ヒマワリ種子_20210511_1133540.txt

The invention claimed is:

1. A sunflower seed comprising a nucleic acid sequence insertion of 400 to 800 nucleotide bases located between a TATA box and a start codon of a stearoyl-acyl carrier protein desaturase 17 (SAD17) gene, wherein the SAD17 gene comprises the nucleotide sequence of SEQ ID NO: 2, wherein the TATA box is located at nucleotides 1-9 of SEQ ID NO: 2 and the start codon is located at nucleotides 122-124 of SEQ ID NO: 2, wherein the sunflower seed has a higher stearic acid content as compared to a sunflower seed without the nucleic acid sequence insertion in the SAD17 gene, wherein the nucleic acid sequence insertion is introduced into a high-oleic acid sunflower line having an oleic acid content of 75 to 90%, and wherein the nucleic acid sequence insertion comprises a nucleotide sequence having at least 80% sequence identity to the nucleotide sequence of SEQ ID NO: 1.

2. The sunflower seed according to claim 1, wherein the nucleic acid sequence insertion comprises at least 90% sequence identity to the nucleotide sequence of SEQ ID NO: 1.

3. The sunflower seed according to claim 1, having a stearic acid content of 11% or more.

4. The sunflower seed according to claim 1, wherein the sunflower seed is homozygous for the nucleic acid sequence insertion.

5. The sunflower seed according to claim 1, which is a seed of the FO-HS43 line or a seed of a line obtained by self-crossing of plants of the FO-HS43 line.

6. A sunflower plant comprising the sunflower seed of claim 1.

7. A sunflower plant obtained by germinating and growing the sunflower seed of claim 1.

8. A method for producing a lipid, comprising collecting a lipid from the sunflower seed of claim 1.

9. The sunflower seed according to claim 2, wherein the nucleic acid sequence insertion comprises the nucleotide sequence of SEQ ID NO: 1.

* * * * *

SEQUENCE LISTING

```
<160> NUMBER OF SEQ ID NOS: 13

<210> SEQ ID NO 1
<211> LENGTH: 586
<212> TYPE: DNA
<213> ORGANISM: Artificial Sequence
<220> FEATURE:
<223> OTHER INFORMATION: insert

<400> SEQUENCE: 1
```

```
taggggtgtt caaaaaactc gtggctcgca gctcgctcga aactcgctcg aaaaaagctc      60

gaagaaagct cggctcgaaa ttggctcggt tgtaaacgag ccagctcggc tcggctcggt     120

ttgtaaacga gccgagctcg agcttggcct ggctcggctc gtgagctcgt gagctggctc     180

gataaggctt acatacttca ttttttttt tgtcccacat cgcttagaaa acaaaaacta     240

agggagtatc tcccctataa aagaaggtaa agacaatgga gaaagtgaat tacctattta     300

tacttgcata tttagccatg tggttaaatt aaatggcaac tatggccctt aggctttgaa     360

gaaattcatt tttaagggct ttttaagtaa taaattttgc ggtactttgt tagttcgagc     420

taaatcgagc cgagccgagc tagctcgaat tcaaatcgag ccgagctcga gcctcaaatc     480

tcagctcgat ttgaaattcg agctcgagcc gagccagctc gaatcgagtt cgagccgagc     540

tcgagctggg tctagctcgg ctcgactcgg ctcgtttaca gcccta                    586


<210> SEQ ID NO 2
<211> LENGTH: 124
<212> TYPE: DNA
<213> ORGANISM: Helianthus annuus

<400> SEQUENCE: 2

tatataaaac atagcaaaat ataagaccat ctgtgctact ctcttctttc tcacttgtgt      60

ggaggaaaac acaactcaaa aaactgtgca acaacaagca cacacaagaa caacatcaac     120

aatg                                                                   124


<210> SEQ ID NO 3
<211> LENGTH: 718
<212> TYPE: DNA
<213> ORGANISM: Artificial Sequence
<220> FEATURE:
<223> OTHER INFORMATION: inserted 5'UTR

<400> SEQUENCE: 3

tatataaaac atagcaaaat ataagaccat ctgtgctact cttaggggtg ttcaaaaaac      60

tcgtggctcg cagctcgctc gaaactcgct cgaaaaaagc tcgaagaaag ctcggctcga     120

aattggctcg gttgtaaacg agccagctcg gctcggctcg gtttgtaaac gagccgagct     180

cgagcttggc ctggctcggc tcgtgagctc gtgagctggc tcgataaggc ttacatactt     240

cattttttt tttgtcccac atcgcttaga aaacaaaaac taagggagta tctcccctat     300

aaaagaaggt aaagacaatg gagaaagtga attacctatt tatacttgca tatttagcca     360

tgtggttaaa ttaaatggca actatggccc ttaggctttg aagaaattca tttttaaggg     420

ctttttaagt aataaatttt gcggtacttt gttagttcga gctaaatcga gccgagccga     480

gctagctcga attcaaatcg agccgagctc gagcctcaaa tctcagctcg atttgaaatt     540

cgagctcgag ccgagccagc tcgaatcgag ttcgagccga gctcgagctg ggtctagctc     600

ggctcgactc ggctcgttta cagccctagc tactctcttc tttctcactt gtgtggagga     660

aaacacaact caaaaaactg tgcaacaaca agcacacaca agaacaacat caacaatg       718


<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4

aacataagtc taagggcata tataaaaca                                        29
```

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
aatttgggag atctgagagg tttcggttga 30

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
gagtccggtg acgcttcaac gggaga 26

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gtggtggggt gaagggcttc ttggta 26

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
caatacggcg acgtttcaat cagacc 26

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
ttggaggggt aaagggcttt ttggtg 26

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tcgactcggc tcgtttacag 20

<210> SEQ ID NO 11
<211> LENGTH: 22
<212> TYPE: DNA
<213> ORGANISM: Artificial Sequence
<220> FEATURE:

```
<223> OTHER INFORMATION: Primer

<400> SEQUENCE: 11

ccattgttga tgttgttctt gt                                            22


<210> SEQ ID NO 12
<211> LENGTH: 396
<212> TYPE: PRT
<213> ORGANISM: Helianthus annuus

<400> SEQUENCE: 12

Met Ala Ile Arg Ile Asn Thr Ala Thr Phe Gln Ser Asp Leu Tyr Arg
1               5                   10                  15

Ser Phe Ala Phe Pro Gln Pro Lys Pro Leu Arg Ser Pro Lys Phe Ala
            20                  25                  30

Met Ala Ser Thr Ile Gly Ser Ala Thr Thr Lys Val Glu Ser Thr Lys
        35                  40                  45

Lys Pro Phe Thr Pro Pro Arg Glu Val His Gln Gln Val Leu His Ser
    50                  55                  60

Met Pro Pro Gln Lys Ile Glu Ile Phe Lys Ser Met Glu Gly Trp Ala
65                  70                  75                  80

Glu Asp Asn Ile Leu Val His Leu Lys Pro Val Glu Lys Cys Trp Gln
                85                  90                  95

Ala Gln Asp Phe Leu Pro Asp Pro Ala Ser Asp Gly Phe Met Glu Gln
            100                 105                 110

Val Glu Glu Leu Arg Ala Arg Ala Lys Glu Ile Pro Asp Asp Tyr Phe
        115                 120                 125

Val Val Leu Val Gly Asp Met Ile Thr Glu Glu Ala Leu Pro Thr Tyr
    130                 135                 140

Gln Thr Met Leu Asn Thr Leu Asp Gly Val Arg Asp Glu Thr Gly Ala
145                 150                 155                 160

Ser Pro Thr Ser Trp Ala Ile Trp Thr Arg Ala Trp Thr Ala Glu Glu
                165                 170                 175

Asn Arg His Gly Asp Leu Leu His Gln Tyr Leu Tyr Leu Ser Gly Arg
            180                 185                 190

Val Asp Met Arg Gln Ile Gln Lys Thr Ile Gln Tyr Leu Ile Gly Ser
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Ile Ser His Gly Asn Thr Ala
225                 230                 235                 240

Arg His Ala Lys Glu His Gly Asp Val Lys Leu Ala Gln Met Cys Gly
                245                 250                 255

Ile Ile Ala Ala Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
    290                 295                 300

Asp Gly Arg Asp Asp Asn Leu Phe Glu Asn Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Ala Asp Leu Thr Gly Leu Ser Gly Glu
            340                 345                 350
```

-continued

```
Gly Arg Lys Ala Gln Asp Tyr Val Cys Gly Leu Ala Pro Arg Ile Arg
        355                 360                 365

Arg Leu Glu Glu Arg Asn Ser Ala Arg Ala Lys Glu Ser Val Asn Val
    370                 375                 380

Pro Phe Ser Trp Ile Phe Asp Arg Glu Val Lys Leu
385                 390                 395


<210> SEQ ID NO 13
<211> LENGTH: 1459
<212> TYPE: DNA
<213> ORGANISM: Helianthus annuus

<400> SEQUENCE: 13

ctcttctttc tcacttgtgt ggaggaaaac acaactcaaa aaactgtgca acaacaagca      60

cacacaagaa caacatcaac aatggcgatt cgcatcaata cggcgacgtt tcaatcagac     120

ctgtatcgtt cattcgcgtt tcctcaaccg aaacctctca gatctcccaa attcgccatg     180

gcttccacca ttggatccgc tacaacgaag gttgaaagca ccaaaaagcc ctttacccct     240

ccaagggagg ttcaccaaca ggtgctacac tcaatgccgc cacaaaagat cgaaatcttc     300

aaatccatgg agggttgggc cgaagataac atattggttc acctaaagcc cgtcgaaaaa     360

tgctggcaag cacaggattt cctaccagat cccgcatctg acggatttat ggaacaagtg     420

gaggaactac gagctcgggc taaggagatt ccggatgatt actttgttgt tttggtggga     480

gatatgatta ctgaagaagc actgcctact taccaaacaa tgcttaatac tcttgatggt     540

gtgcgtgatg agaccggggc tagccctact tcttgggcta tctggactcg ggcttggacc     600

gctgaagaaa acaggcacgg tgatcttcta catcagtatc tgtatcttag tgggcgggtc     660

gacatgaggc agattcagaa gacaattcag tacctcattg ggtctggaat ggacccccgg     720

actgaaaaca gtccttacct tgggttcatc tacacttcat ttcaagagcg tgccaccttc     780

atctctcacg gaaacacagc ccggcacgca aaggagcatg gtgacgtgaa gctggctcaa     840

atgtgcggta taattgcagc tgatgaaaaa aggcacgaaa ccgcctacac aaaaatagta     900

gaaaaactct tcgaaattga cccggacggc actgttctcg cttttgctga catgatgagg     960

aaaaagatct ccatgcctgc acacttgatg tacgatgggc gtgacgataa cctcttcgaa    1020

aatttctcag ctgttgccca aaggctcggt gtgtacactg caaaggacta tgcagacatt    1080

ctggagtttc tggtgggccg gtggaaggtg gcggatttaa ccgggctttc tggtgaaggg    1140

cgtaaagccc aagactatgt gtgcgggctg gccccaagaa tcagaaggct tgaggagagg    1200

aactcggcaa gggcgaagga aagtgtgaac gttccgttca gctggatctt tgatagagaa    1260

gtgaagctct gaaagttgct atagtaagtt gttaaaacct atattagatt gtcgtttctt    1320

tcgtgtagtg ctgatatgtg ttttcttctc gactttgtaa tgtgtctcga gttcgggtgt    1380

ttgtaaactt gttggacata ttataaaact tgttatgcca gttttgatga cgattatcgt    1440

ctcatcggtc ggttgcaga                                                 1459
```